(12) United States Patent
Wang et al.

(10) Patent No.: US 11,284,926 B2
(45) Date of Patent: Mar. 29, 2022

(54) INTERNAL FIXATION SYSTEM OF MULTI-FUNCTION ADJUSTABLE SPINE POSTERIOR SCREW-ROD

(71) Applicant: Central South University Xiangya Hospital, Changsha (CN)

(72) Inventors: Xiyang Wang, Changsha (CN); Zheng Liu, Hengyang (CN); Yilu Zhang, Changsha (CN); Yunqi Wu, Kunming (CN); Zhenchao Xu, Yiyang (CN); Weiwei Li, Changsha (CN); Zhicheng Sun, Yiyang (CN); Yilin Wang, Changsha (CN); Zhen Zhang, Chongqing (CN); Dingchao Rong, Yongzhou (CN); Hongru Ye, Changsha (CN); Xiao Xiao, Changsha (CN)

(73) Assignee: Central South University Xiangya Hospital, Changsha (CN)

( * ) Notice: Subject to any disclaimer, the term of this patent is extended or adjusted under 35 U.S.C. 154(b) by 188 days.

(21) Appl. No.: 16/541,168

(22) Filed: Aug. 15, 2019

(65) Prior Publication Data
US 2021/0045782 A1 Feb. 18, 2021

(51) Int. Cl.
*A61B 17/70* (2006.01)
*A61B 17/80* (2006.01)
*A61B 17/88* (2006.01)

(52) U.S. Cl.
CPC ...... *A61B 17/7059* (2013.01); *A61B 17/7002* (2013.01); *A61B 17/7043* (2013.01); *A61B 17/7049* (2013.01); *A61B 17/7058* (2013.01); *A61B 17/8033* (2013.01); *A61B 17/8802* (2013.01)

(58) Field of Classification Search
CPC ............ A61B 17/7049; A61B 17/7058; A61B 17/7059; A61B 17/7061; A61B 17/7062; A61B 17/7068
See application file for complete search history.

(56) References Cited

U.S. PATENT DOCUMENTS

| 5,437,672 | A  | * | 8/1995  | Alleyne | A61B 17/00   |
|           |    |   |         |         | 606/279      |
| 10,952,856| B2 | * | 3/2021  | Freese  | A61B 17/7043 |
| 2009/0326592 | A1 | * | 12/2009 | Butler | A61B 17/7058 |
|           |    |   |         |         | 606/286      |

(Continued)

*Primary Examiner* — Nicholas W Woodall
(74) *Attorney, Agent, or Firm* — McClure, Qualey & Rodack, LLP

(57) ABSTRACT

The invention provides the internal fixation system of multi-function adjustable spine posterior screw-rod. It not only includes the vertebral plate, but also includes the adjustable connecting rod, screw and lock nut. Among them, vertebral plate is curved, its internal cambered surface directly faces the spine, and external cambered surface of vertebral plate is equipped with a reinforcing rib. The vertebral plate is set with the perforative injecting hole, and the external cambered surface of vertebral plate is set with the located block. The surface of the located block is set with the concave threaded hole, and the located block on two sides of the threaded hole is set with the U-shaped bracket. The top of screw expands to form a locking block, which surface is set with the concave locking hole. The locking block on both sides of locking hole is set with the U-shaped locking groove.

4 Claims, 6 Drawing Sheets

(56) References Cited

U.S. PATENT DOCUMENTS

Figure 1:
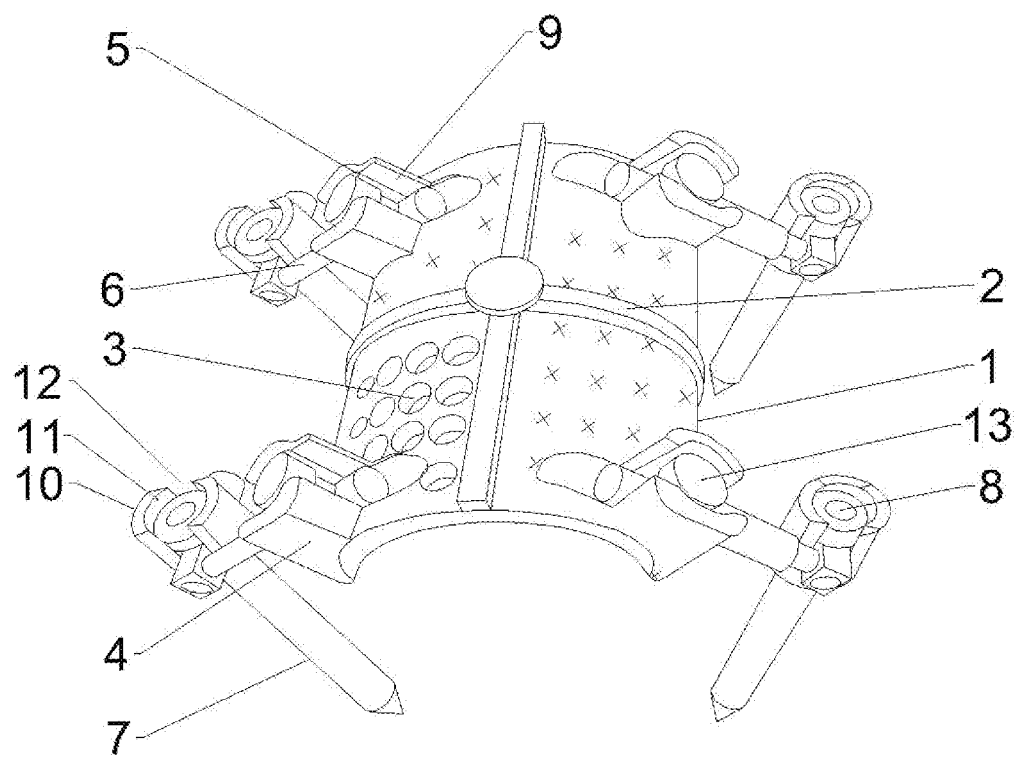

| | | | | |
|---|---|---|---|---|
| 2010/0174315 A1* | 7/2010 | Scodary | ............. | A61B 17/7052 |
| | | | | 606/248 |
| 2012/0158060 A1* | 6/2012 | Abrahams | .......... | A61B 17/7065 |
| | | | | 606/248 |
| 2014/0052183 A1* | 2/2014 | Freese | ................ | A61B 17/0401 |
| | | | | 606/248 |
| 2017/0119439 A1* | 5/2017 | Ozdil | .................. | A61B 17/7052 |
| 2017/0325852 A1* | 11/2017 | Chen | .................... | A61B 17/705 |
| 2021/0045780 A1* | 2/2021 | Zhu | .................... | A61B 17/7032 |

* cited by examiner

INTERNAL FIXATION SYSTEM OF MULTI-FUNCTION ADJUSTABLE SPINE POSTERIOR SCREW-ROD

TECHNICAL FIELD

The invention involves the field of surgical medical equipment, especially the internal fixation system of multi-function adjustable spine posterior screw-rod.

BACKGROUND TECHNOLOGY

Most of the existing vertebral plate is elongated, which is fixed on both sides of the spine after operation. This method is to first place the vertebral plate against the spine, lock a connecting rod on each side of the vertebral plate, then insert the steel pin according to the position of connecting rod, and then fix the vertebral plate. The operation is tedious, and the connecting rod occupies a large area, which isn't easy for subsequent operation.

Contents of the Invention

The purpose of the invention is to overcome the deficiency of the current technology and to provide the internal fixation system of multi-function adjustable spine posterior screw-rod with good positioning effect and convenient operation.

To realize the above purposes, the technical scheme which is provided by the invention is as follows: the internal fixation system of multi-function adjustable spine posterior screw-rod not only includes the vertebral plate, but also includes the adjustable connecting rod, screw and lock nut. Among them, vertebral plate is curved, its internal cambered surface directly faces the spine, and external cambered surface of vertebral plate is equipped with a reinforcing rib. The vertebral plate is set with the perforative injecting hole, and four corners of the external cambered surface of vertebral plate extend upward to form the located block, which surface is set with the concave threaded hole, and the located block on two sides of the threaded hole is set with the U-shaped bracket. The top of screw expands to form a locking block, which surface is set with the concave locking hole. The locking block on both sides of locking hole is set with the U-shaped locking groove. One end of adjustable connecting rod is located in the threaded hole. The adjustable connecting rod in the threaded hole is locked by the adjusting nut. The other end of adjustable connecting rod is put in the locking groove through the bracket, and adjustable connecting rod in the locking groove is locked through the lock nut.

The mentioned adjustable connecting rod is L-shaped, and its corners are hinged by the hinge pin.

The mentioned diameter of the adjustable connecting rod is less than the width of bracket and locking groove.

The mentioned reinforcing rib humps on the surface of the vertebral plate in the form of "cross", and extends to form a cylinder at the central intersection, and the injecting hole is distributed in a matrix on the vertebral plate.

The above scheme is used in the invention. According to the position where the spine shall be fixed, place the screw on the body on both sides of the spine, insert one end of the adjustable connecting rod into the threaded hole, and lock by the adjusting nut. Rotate the other end (movable arm) of adjustable connecting rod according to the positions of the screw, place the other end of the adjustable connecting rod (movable arm) in the locking groove through the bracket, and then lock by the lock nut. The occupied position of adjustable connecting rod and screw is small after locking in this way, which doesn't affect other any operation. At the same time, the adjustable area is large after the L-shaped adjustable connecting rod is adopted. The diameter of adjustable connecting rod is less than the width of bracket and locking groove, which can make the adjustable connecting rod rotate in the bracket and locking groove at a certain angle. After rotating in place, it is locked by the corresponding nut. Its positioning effect is good, and operation is convenient.

INSTRUCTION WITH DRAWINGS

Figure 2:
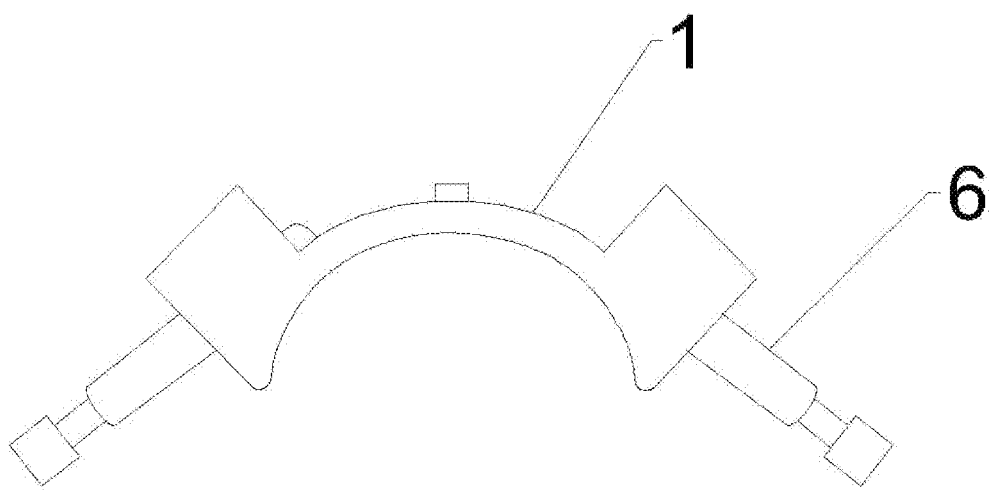
Figure 3:
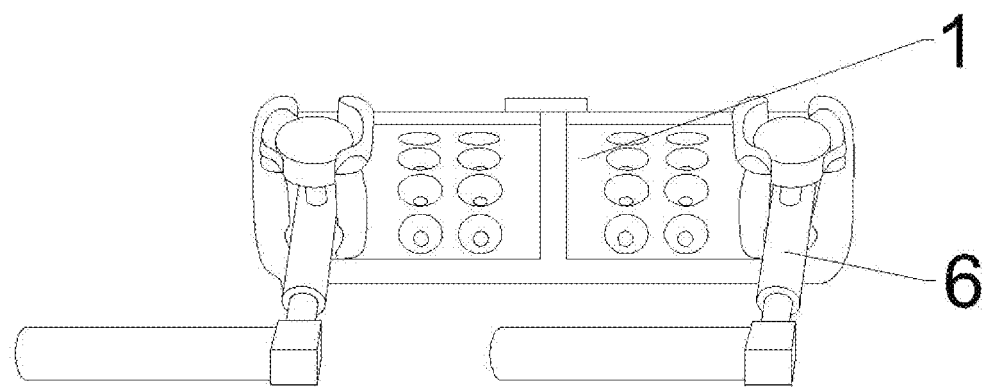
Figure 4:
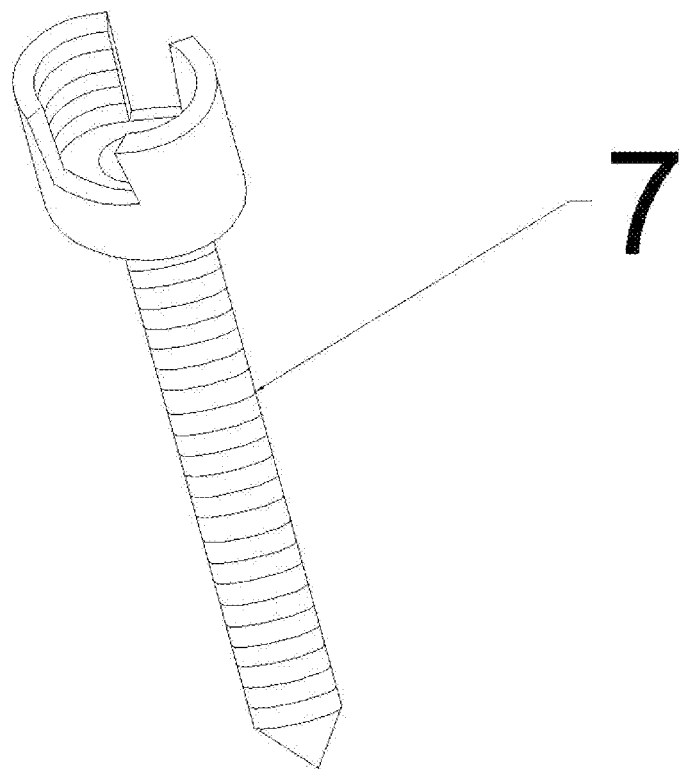
Figure 5:
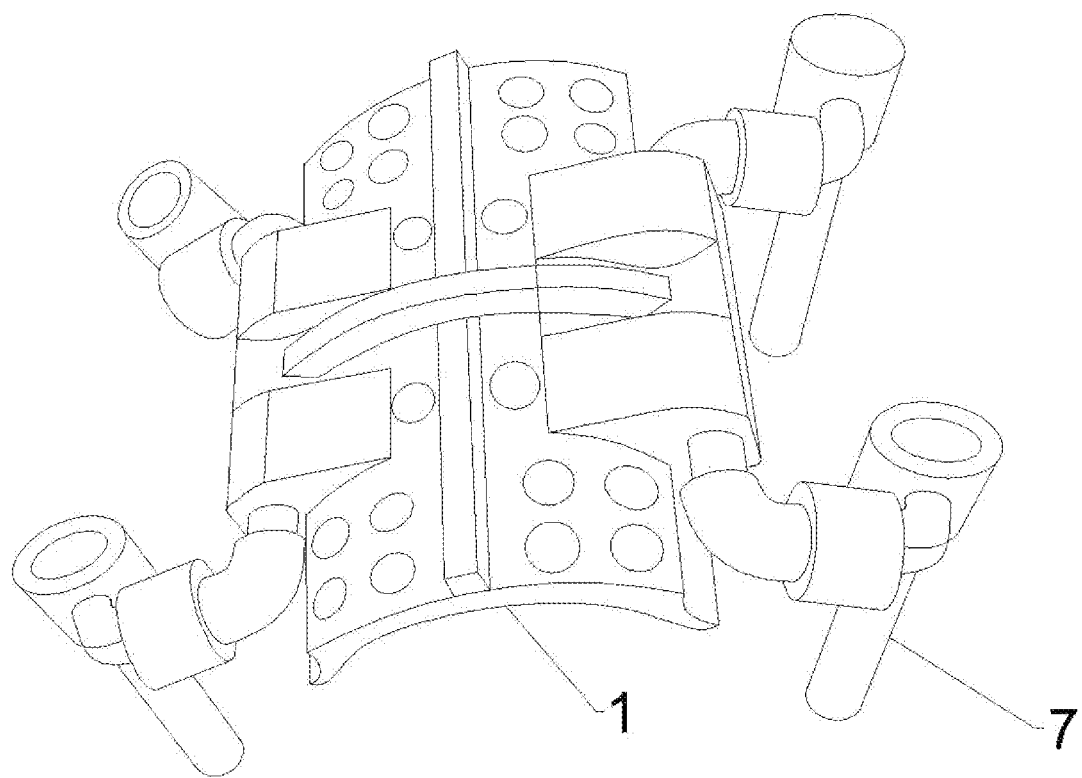
Figure 6:
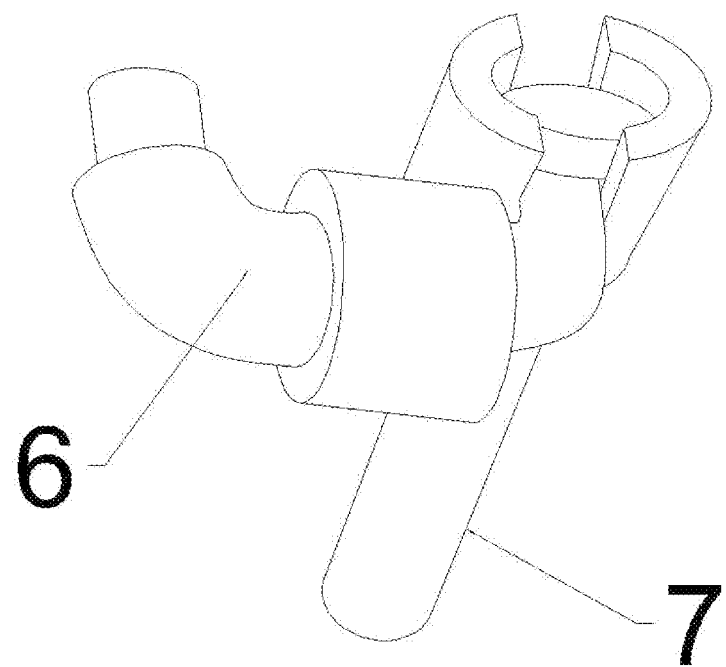

FIG. 1 is the overall structure schematic diagram of the invention.
FIG. 2 is the end schematic diagram of the invention.
FIG. 3 is the side schematic diagram of the invention.
FIG. 4 is the screw schematic diagram of the invention.
FIG. 5 is the hinge joint schematic diagram of adjustable connecting rod of the invention.
FIG. 6 is a schematic diagram of the fixed L-shaped adjustable connecting rod of the invention.

SPECIFIC IMPLENTATION MODE

The invention is further described in combination with all the attached drawings. Refer to the attached drawings 1 to 4 for the better embodiment of the invention.

In the embodiment, the internal fixation system of multi-function adjustable spine posterior screw-rod not only includes the vertebral plate 1, but also includes the adjustable connecting rod 6, screw 7 and lock nut 8. Among them, vertebral plate 1 is curved, its internal cambered surface directly faces the spine, and external cambered surface of vertebral plate 1 is equipped with a reinforcing rib 2. The vertebral plate 1 is set with the perforative injecting hole 3. The reinforcing rib 2 humps on the surface of the vertebral plate 1 in the form of "cross", the reinforcing rib 2 extends to form a cylinder at the central intersection, and the injecting hole 3 is distributed in a matrix on the vertebral plate 1. Four corners on the external cambered surface of vertebral plate 1 extend upward to form the located block 4, which surface is set with the concave threaded hole 5, and the located block 4 on two sides of the threaded hole 5 is set with the U-shaped bracket 9; the top of screw 7 expands to form a locking block 10, which surface is set with the concave locking hole 11. The locking block 10 on both sides of locking hole 11 is set with the U-shaped locking groove 12. One end of adjustable connecting rod 6 is located in the threaded hole 5. The adjustable connecting rod 6 in the threaded hole 5 is locked by the adjusting nut 13. The other end of adjustable connecting rod 6 is put in the locking groove 12 through the bracket 9, and adjustable connecting rod 6 in the locking groove 12 is locked by the lock nut 8. The adjustable connecting rod 6 is L-shaped, and its corners are hinged by the hinge pin. The diameter of the adjustable connecting rod 6 is less than the width of bracket 9 and locking groove 12.

In the embodiment, place the screw on the body on both sides of the spine according to the position where the spine shall be fixed, insert one end of the adjustable connecting rod into the threaded hole, and lock by the adjusting nut. Rotate the other end (movable arm) of adjustable connecting rod according to the positions of the screw, place the other end of the adjustable connecting rod (movable arm) in the locking groove through the bracket, and then lock by the lock nut. The occupied position of adjustable connecting rod and screw is small after locking in this way, which doesn't affect other any operation. At the same time, the adjustable area is large after the L-shaped adjustable connecting rod is adopted. The diameter of adjustable connecting rod is less than the width of bracket and locking groove, which can make the adjustable connecting rod rotate in the bracket and locking groove at a certain angle. After rotating in place, it is locked by the corresponding nut. Its positioning effect is good, and operation is convenient.

In addition, the adjustable connecting rod may be set to the structure shown in FIG. 5 and FIG. 6 according to the requirements, which is convenient for special patients.

The above embodiment is only better embodiment of the invention and doesn't limit the implementation scope of the invention, so the changes that are made according to the shape and principle of the invention shall be covered in the protection scope of the invention.

We claim:

1. An internal fixation system of multi-function adjustable spine posterior screw-rod, comprising
    a vertebral plate (1), wherein the vertebral plate (1) is curved, an internal cambered surface of the vertebral plate (1) directly faces a spine, and an external cambered surface thereof is equipped with reinforcing ribs (2); the vertebral plate (1) is provided with at least one injecting hole (3), and four corners of the external cambered surface of the vertebral plate (1) extend upwards to form located blocks (4), and surfaces of the located blocks (4) are provided respectively with a concave threaded hole (5), and the located blocks (4) on both sides of the threaded holes (5) are provided with U-shaped indented brackets (9);
    at least one lock nut (8);
    at least one adjustable connecting rod (6), wherein one end of the at least one adjustable connecting rod (6) is respectively located in the threaded holes (5), and the at least one adjustable connecting rod (6) in the threaded holes (5) are respectively locked by at least one adjusting nut (13), another end of the at least one adjustable connecting rod (6) is put in the at least one U-shaped locking groove (12) through the indented brackets (9), and the at least one adjustable connecting rod (6) in the at least one U-shaped locking grooves (12) is respectively locked through the at least one lock nut (8); and
    at least one screw (7), wherein a top portion of the at least one screw (7) expands to form respectively a locking block (10), on a top surface of the locking block (10) is provided an indented locking hole (11), and the locking block (10) on both sides of the locking hole (11) is provided with at least one U-shaped locking groove (12).

2. The internal fixation system of multi-function adjustable spine posterior screw-rod according to claim 1, wherein: the at least one adjustable connecting rod (6) is L-shaped, and a corner thereof is hinged by at least one hinge pin.

3. The internal fixation system of multi-function adjustable spine posterior screw-rod according to claim 1, wherein: a diameter of the at least one adjustable connecting rod (6) is less than a width of each of the indented brackets (9) and a width of the at least one locking groove (12).

4. The internal fixation system of multi-function adjustable spine posterior screw-rod according to claim 1, wherein: the reinforcing ribs (2) humps on a surface of the vertebral plate (1) in a form of "a cross", a cylinder is formed at an intersection of the reinforcing ribs (2), and the at least one injecting hole (3) is distributed in a matrix on the vertebral plate (1).

* * * * *